United States Patent [19]

Simon et al.

[11] Patent Number: 4,997,625

[45] Date of Patent: Mar. 5, 1991

[54] CHEMICAL STERILIZATION

[76] Inventors: Gilbert I. Simon, 1111 Midland Ave., Bronxville, N.Y. 10708; Roy T. Witkin, 23 Broadview Rd., Westport, Conn. 06880

[21] Appl. No.: 835,378

[22] Filed: Mar. 3, 1986

Related U.S. Application Data

[62] Division of Ser. No. 763,469, Aug. 7, 1985, Pat. No. 4,923,677.

[51] Int. Cl.$^5$ ............... A61L 2/18; A61K 33/18; A61K 33/40
[52] U.S. Cl. ............... 422/29; 422/28; 422/37; 424/616; 424/672
[58] Field of Search ............... 422/12, 28, 29, 37, 422/616, 672; 424/130, 150

[56] References Cited

U.S. PATENT DOCUMENTS

| | | | |
|---|---|---|---|
| 4,113,857 | 9/1978 | Shetty | 424/150 |
| 4,521,403 | 6/1985 | Simon et al. | 424/150 X |
| 4,526,751 | 7/1985 | Gartner | 424/150 X |
| 4,567,036 | 1/1986 | Simon et al. | 424/150 X |
| 4,592,487 | 6/1986 | Simon et al. | 222/94 |
| 4,592,488 | 6/1986 | Simon et al. | 222/94 |
| 4,592,489 | 6/1986 | Simon et al. | 222/94 |

FOREIGN PATENT DOCUMENTS

| | | | |
|---|---|---|---|
| 8423635 | 7/1984 | Austria | 424/130 |
| 2438594 | 2/1976 | Fed. Rep. of Germany | 424/150 |
| 2718385 | 11/1978 | Fed. Rep. of Germany | 424/150 |

OTHER PUBLICATIONS

U.S. EPA Pesticide Guidelines, Subdivision G, *Product Performance* (Nov. 1982, PB83-153924), Section 91-3-0-5, "Disinfection Efficacy Against Viruses."
Kirk-Othmer, Encyclopedia of Chemical Technology, 3(7), pp. 802, 803; (13), pp. 649-655, 660-662, 673, 674.

*Primary Examiner*—Robert J. Warden
*Assistant Examiner*—Jill Johnston
*Attorney, Agent, or Firm*—Jacobs & Jacobs

[57] ABSTRACT

Dental and medical instruments and appliances are chemically sterilized by immersion in or subjection to a formulation or composition comprising as active antimicrobial agents a combination or admixture of an iodophor such as the povidone-iodine complex or a quaternary ammonium compound such as cetyl pyridinium chloride and a peroxide such as $H_2O_2$, the antimicrobial action of the iodine derived from the iodophor being enhanced or potentiated by oxygen released from the peroxide. The invention is applicable also to the chemical sterilization of surgical sites. Procedure for making and using the sterilizing formulation or composition is described.

9 Claims, No Drawings

CHEMICAL STERILIZATION

CROSS-REFERENCE

This is a division of Ser. No. 763,469 filed Aug. 7, 1985 now U.S. Pat. No. 4,923,677.

The present invention relates to sterilization and more particularly to chemical sterilization for rendering dental and medical instruments and appliances and actual and potential surgical sites sterile and free from live microbials.

Dental and medical instruments and appliances during use become unavoidably contaminated or soiled by microbials, both pathogens and non-pathogens such as bacteria, yeast, fungi and viral matter and before those dental and medical instruments and appliances can be used or re-used they must be treated to make them free from microbial, viral and other forms of contamination such as blood, tissue and mucus. Many of such dental and medical instruments and appliances are made of expensive steels and alloys and it is thus desired to keep them ready for continued use since it would be uneconomical and wasteful to have to replace them with new sterile instruments and appliances after each use.

The usual practice in the sterilization of various metal and alloy instruments and appliances has been to subject them to autoclaving, at the temperature of a hot-air oven or boiling water to destroy or remove live microorganisms and spores. Other procedures are carried out by sound, gases, e.g. ethylene oxide, light and $\gamma$-ray irradiation or sometimes by disinfectant iodine solutions. While such practices may be generally satisfactory, the usual thermal or conventional procedure leaves open the possibility of incomplete or inconvenient time-consuming sterilization and the requirement for special equipment and experienced personnel.

In accordance with the present invention, dental and medical instruments and appliances of the usual nature employed in dental and medical practice are sterilized by means of simple, inexpensive commercially available chemicals having together exceptional antimicrobial and viricidal properties at ambient temperature and atmospheric conditions, and sterilization need only be carried out for a short period of time, e.g. 5 minutes, thereby avoiding the disadvantages and expense of thermal autoclaving or other prior known sterilizing procedures. More particularly, the chemical sterilization is carried out by immersing in or otherwise physically subjecting the dental and medical instruments and appliances to an antimicrobial solution admixture which comprises as its major active components an iodophor such as the povidone-iodine complex (PVP-I) and $H_2O_2$, the iodine derived from the PVP-I being potentiated or enhanced in its antimicrobial activity by the active or nascent oxygen from the peroxide. This combination of PVP-I and $H_2O_2$ solutions maximizes the antimicrobial activity and shortens the time required for sterilization.

We have found that when dental and medical instruments and appliances require sterilization, such can be quickly and inexpensively carried out by means of an antimicrobial solution containing PVP-I and $H_2O_2$ or other peroxy compound such as carbamide peroxide or benzoyl peroxide, wherein the PVP-I as a source of derived iodine and the peroxide as a source of oxygen are preferably but not necessarily present in predetermined relative proportions to provide enhanced or potentiated antimicrobial and viricidal activity. Such a solution, which is an admixture of the PVP-I and the peroxide, has been found to have surprising and unexpected enhanced antimicrobial activity against gram-positive and gram-negative bacteria and bacterial viruses and other microbial contaminants so that the admixture has a wide effective spectrum of antimicrobial activity for sterilization purposes.

According to the invention and illustrative of sterilization against the bacterial virus T-7, viricidal activity of multiple combinations of PVP-I and $H_2O_2$ were conducted to demonstrate maximized activity by the method described in U.S. EPA Pesticide Assessment Guidelines Subdivision G: *Product Performance* (November 1982; PB83-153924) Section 91-30-5-"Disinfection Efficacy Against Viruses", which procedure determines the reduction in viral titre after a five minute exposure to the agent. Each such determination was carried out in quadruplicate.

Stock solutions of $H_2O_2$ (35% $H_2O_2$ Dupont Albone 35 CG) and PVP-I (20% PVP-I solution having 2.2% available iodine) were diluted in sterile distilled water to the desired concentrations just prior to experimentation.

To microtitre plate wells, 10 $\mu$L of virus suspension ($10^{6-7}$ VP/ml in 5% fetal calf serum) were added and allowed to air dry. An aliquot (28 $\mu$L) of $H_2O_2$, PVP-I or combination was added to wells containing the dried virus and contacted for 5 minutes, after which the aliquot was withdrawn and placed into another microtitre plate whose wells contained 250 $\mu$L nutrient broth which was previously inoculated with the virus host, *Escherichia coli* bacteriophage (ATCC 5177). Serial dilutions (1:10) were carried out in this plate until the viral inoculum was diluted $10^8$ times. Viral viability was determined by lysis of the viral host, i.e., the absence of bacterial growth as measured by absorbance at 450 $\mu$m.

Toxicity of the $H_2O_2$, PVP-I and combinations thereof to the host organism was also determined.

TABLE 1

Relationship of T-7 Titre Reduction (in logs) to Various Concentrations of PVP-I and $H_2O_2$ Singly and in Combination

| PVP-I (%) | $H_2O_2$ (%) | Log Reduction |
| --- | --- | --- |
| 0 | $\geq 6$ | 0 |
| 0.2 | 0 | 1 |
| 0.1 | 0 | $\geq 1$ |
| 0.1 | 3 | 3 |
| 0.15 | 3 | 4 |
| 0.15 | 1.5 | 3 |

The above table shows the degree of viral kill as measured in log reduction of viral titre after exposure various concentrations and combinations of $H_2O_2$ and PVP-I, the concentrations of PVP-I in all instances being as percent of available iodine. Enhancement or potentiation of activity was determined to exist if the PVP-I/$H_2O_2$ combinations exhibited a greater than expected degree of viricidal activity than was observed by the use of the agents singly or additively and as will be noted from Table 1, the degree of viricidal activity of the PVP-I/$H_2O_2$ combinations is greater than their individual activities or their merely additive activities and hence the combinations showed enhanced or potentiated activity.

TABLE 2

Viricidal Concentrations of PVP-I and $H_2O_2$
Singly and in Combination Against Bacteriophage
T-7 That Show a 4 Log Reduction in Virus Titre

| PVP-I Conc. (%) | $H_2O_2$ Conc. (%) |
|---|---|
| 0.3 | 0 |
| 0.15 | 3 |
| 0 | 12 |

The concentrations of PVP-I and $H_2O_2$ singly and in combination in Table 2 further demonstrate the attainment of enhanced or potentiated activity for the PVP-I/$H_2O_2$ combination, as indicated by a 4 log reduction in viral titre.

It is further to be understood that the present invention relates not only to the chemical sterilization of dental and medical instruments and appliances used by dentists, dental surgeons, physicians and surgeons, but that it also includes the application of the sterilizing aqueous or aqueous alcoholic solutions or formulations to surgical sites by washing, spraying or swabbing whether the surgical sites result from use of the instruments and appliances or whether skin or body areas are to be sterilized preparatory to surgery. In the normal use of dental and surgical instruments and appliances there may well be resultant surgical sites as from incisions or operations which require treatment to prevent infection or the spread of infection.

For this purpose the same compositions or solutions are utilized as for the chemical sterilization of the instruments and appliances themselves, i.e. a composition of an iodophor such as PVP-I and a peroxy compound releasing oxygen for enhancing or potentiating the antimicrobial activity of the iodine derived from the iodophor. The active or nascent oxygen released from $H_2O_2$ or other peroxide has been found to markedly increase the antimicrobial effectiveness of the iodine derived from PVP-I, and in the chemical sterilization of the instruments and appliances, the iodophor and the source of oxygen are preferably but not necessarily present in predetermined relative proportions, so long as the relationship gives a maximal peak of activity for sterilization purposes. The sterilizing composition or solution is initially in the form of separate components or solutions which are maintained out of physical contact with one another until it is desired to combine and use the same for sterilization purposes, or the components may be premixed in a suitable dual compartmented or partitioned container or vessel and discharged together just shortly before use at ambient temperature and atmospheric conditions. When freshly combined the PVP-I and $H_2O_2$ solutions have the maximal sterilizing activity in the shortest period of time.

The surgical sites are treated by applying the admixed components thereto and this may be carried out by means of a swab, spray or applicator and, if necessary, the site covered by a bandage to assist in healing while at the same time preventing access of undesirable contaminants to such treated sites. The particular manner and formulation of application of the antimicrobial components or solutions may be varied, depending upon the nature and extent of the surgical site and its location on or in a human body. For this purpose, the chemical sterilizing components or solutions may be formulated into a lotion, paste, gel, ointment, spray, cream or surgical scrub especially where the surgical site is in a location to which an aqueous solution might not adhere for a sufficient length of time to ensure complete sterilization. The sterilizing compositions may also be formulated as a vaginal or rectal douche or suppository when the surgical sites or infections are located in those areas.

It is further understood that the invention, whether used to sterilize dental and surgical instruments and appliances or to be applied to surgical sites, may further comprise an iodophor such as PVP-I or other nonoxynol surfactant carrier or complexing agent for iodine, e.g. Biopal (GAF Corp.), and further may include alternative suitable sources of active or nascent oxygen other than $H_2O_2$, such as carbamide peroxide and benzoyl peroxide. Sodium chlorite, which is a source of chlorine dioxide $ClO_2$, may be included as an oxygen source.

The basic materials or non-active components in compositions for chemical sterilization according to the present invention, exclusive of the iodophor and peroxide, when not in aqueous or aqueous alcoholic solution form, are formulated with the usual or conventional ingredients in known manner to form pastes, gels, lotions, ointments, creams, sprays, surgical scrubs and other semi-liquid or semi-solid formulations or to form rectal and vaginal douches, enemas or suppositories so long as the active components are present in suitable proportions for effective antimicrobial activity. The non-active components per se form no part of the present invention. Typical formulations of the above types involving PVP-I are published in BASF publication 30/06 Register 4 of 09/80.

The PVP-I is incorporated into one portion of each such formulation and the $H_2O_2$ is incorporated into another like portion and the portions are admixed just prior to their use, or they may be formulated and premixed in a suitable dual compartmented or partitioned receptacle or container from which they are discharged together shortly before use.

In the preferred manner of practicing the invention, used or post-operative dental and surgical instruments and appliances are cleansed of all organic matter such as blood, tissue and mucus by detergent washing or ultrasonically to remove all debris following which the instruments and appliances are rinsed sterilized as above described by immersion or subjection to the chemical sterilizing solutions or compositions. Thereafter, the now sterilized instruments and appliances are removed from the sterilizing solutions or compositions, rinsed with sterile water to ensure complete removal of any residual matter and placed under or between sterile towels and permitted to dry.

In utilizing the aqueous or aqueous alcoholic forms of sterilization, the available iodine need be only about 2% in the case of instruments and appliances, whereas solutions for the treatment of surgical sites need have only about 1% available iodine for effective sterilization. The concentration of an $H_2O_2$ or other peroxide solution as a source of nascent or active oxygen is not critical relative to the available iodine so long as enough oxygen is released to interact with or upon at least an appreciable part of the available iodine to enhance or potentiate the antimicrobial activity of the available iodine. This iodine/oxygen relation can be 1:1 v/v but can also be less such as one-tenth to one-half oxygen ratio relative to the iodine percentage.

Other and further variations and modifications of the invention may be made as will be appreciated by dental and surgical technicians without departing from the scope or concept of the invention as defined by the sub-joined claims.

What is claimed is:

1. A method of enhanced chemical sterilization of existing and potential surgical sites resulting from the use or intended use of dental and surgical instruments and appliances on an area of the human body operated upon or to be operated thereon which comprises subjecting for a sufficient period of time to effect sterilization the surgical sites to be sterilized to the action of a potentiated antimicrobial aqueous solution comprising an iodophor component as a source of iodine and a peroxide component as a source of active or nascent oxygen, the antimicrobial activity of the iodine of the iodophor component being antimicrobially potentiated by oxygen of the peroxide component when the two components are admixed to form the antimicrobial solution and the surgical sites subjected to sterilization therewith.

2. A method according to claim 1 wherein the iodophor component is povidone iodine and the peroxide component is $H_2O_2$.

3. A method according to claim 1 wherein the sterilization of the surgical sites is carried out by applying the potentiated antimicrobial solution to the skin areas to be sterilized.

4. A method according to claim 3 wherein the sterilization of the surgical sites is carried out with a swab or spray.

5. A method of chemically sterilizing existing or potential surgical sites on a human body part which comprises applying to the sites an effective amount of an aqueous antimicrobial solution of povidone iodine and an aqueous solution of a peroxide, the povidone iodine being a source of iodine which is potentiated in its antimicrobial action by the active or nascent oxygen of the peroxide, the solutions being maintained out of contact with one another until sterilization is to be carried out whereupon the solutions are combined and applied to the sites.

6. A method according to claim 5 wherein the povidone iodine and the peroxide are separately dissolved in water out of contact with one another and then admixed and the admixture applied to the sites.

7. A method of chemically sterilizing body surface areas constituting surgical sites which comprises preparing an antimicrobial aqueous solution of an iodophor, preparing a separate aqueous solution of a peroxide, maintaining the solutions out of contact with one another, introducing predetermined relative amounts of said solutions into a common receptacle in which the solutions become admixed, promptly applying the admixed solutions to the surgical sites, said admixed solutions interacting with each other so that oxygen released from the peroxide solution potentiates the antimicrobial activity of the iodine derived from the iodophor solution, whereupon the thus treated surgical sites are rendered free of bacterial and viral contamination.

8. A method according to claim 7 wherein the iodophor is povidone iodine and the peroxide is hydrogen peroxide.

9. A method of chemically sterilizing surgical sites according to claim 7 wherein the available iodine of the povidone iodine solution is approximately 1%-2%.

* * * * *